United States Patent
Ehrhorn

(10) Patent No.: US 7,741,950 B2
(45) Date of Patent: Jun. 22, 2010

(54) HUMIDITY SENSOR AND A METHOD FOR MANUFACTURING THE SAME

(75) Inventor: Kristian Ehrhorn, Odense S (DK)

(73) Assignee: Senmatic A/S, Sonderso (DK)

( * ) Notice: Subject to any disclaimer, the term of this patent is extended or adjusted under 35 U.S.C. 154(b) by 624 days.

(21) Appl. No.: 11/577,338

(22) PCT Filed: Oct. 17, 2005

(86) PCT No.: PCT/DK2005/000667
§ 371 (c)(1),
(2), (4) Date: Apr. 16, 2007

(87) PCT Pub. No.: WO2006/042546
PCT Pub. Date: Apr. 27, 2006

(65) Prior Publication Data
US 2008/0048822 A1  Feb. 28, 2008

(30) Foreign Application Priority Data
Oct. 18, 2004  (DK) .............................. 2004 01590

(51) Int. Cl.
*H01C 7/00* (2006.01)
(52) U.S. Cl. .................. 338/35; 338/34; 73/335.05; 324/674; 361/286
(58) Field of Classification Search .............. 338/34, 338/35; 73/335.05, 29.01, 29.05; 361/286; 324/674, 289; 252/963
See application file for complete search history.

(56) References Cited

U.S. PATENT DOCUMENTS

| 4,562,725 | A | | 1/1986 | Oka et al. |
| 4,856,320 | A | | 8/1989 | Bose et al. |
| 4,900,405 | A | * | 2/1990 | Otagawa et al. .............. 205/781 |
| 5,608,374 | A | * | 3/1997 | Ikejiri ........................... 338/35 |
| 5,777,206 | A | * | 7/1998 | Zuchner et al. ............. 73/29.01 |
| 6,812,821 | B2 | * | 11/2004 | Fujita et al. .................... 338/34 |
| 6,840,103 | B2 | * | 1/2005 | Lee et al. .................. 73/335.05 |
| 2002/0173922 | A1 | | 11/2002 | Potyrailo |

* cited by examiner

Primary Examiner—Kyung Lee
(74) Attorney, Agent, or Firm—Fitch, Even, Tabin & Flannery

(57) ABSTRACT

The invention relates to a humidity sensor comprising a sensor element, a molding, which preferably consists of a thermoplastic material or a two-component polyurethane, epoxy or silicone casting and which is adapted to adhere to the sensor element, a dead-space volume, which is arranged in connection with the sensor element and which is covered by a membrane. The membrane is attached to an external surface of the molding and is adapted to protect the sensor element from exposure to ambient moisture and dirt and allowing diffusion of ambient air gas molecules, like water vapor, into the dead-space volume. The dead-space volume is less than 100 mm$^3$.

11 Claims, 1 Drawing Sheet

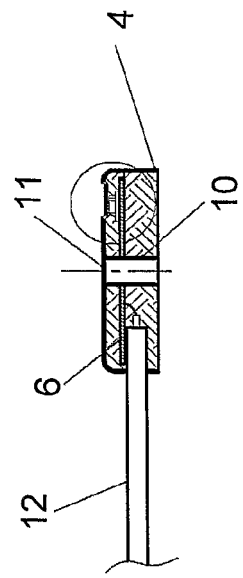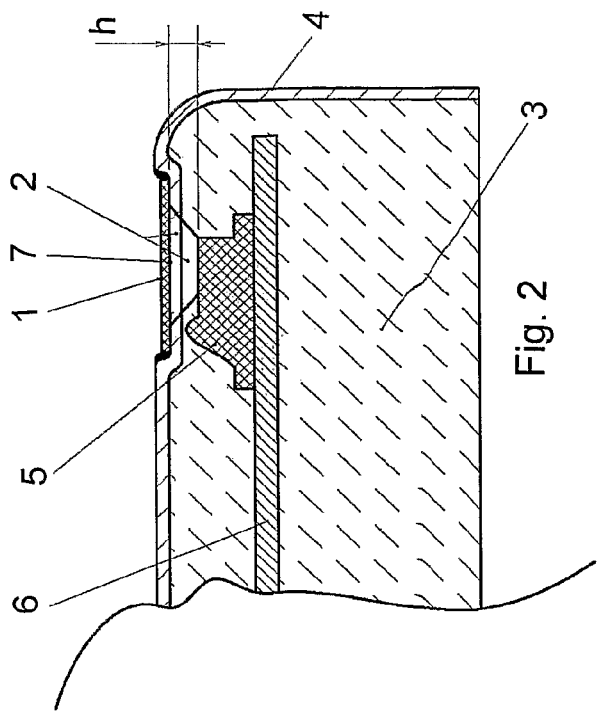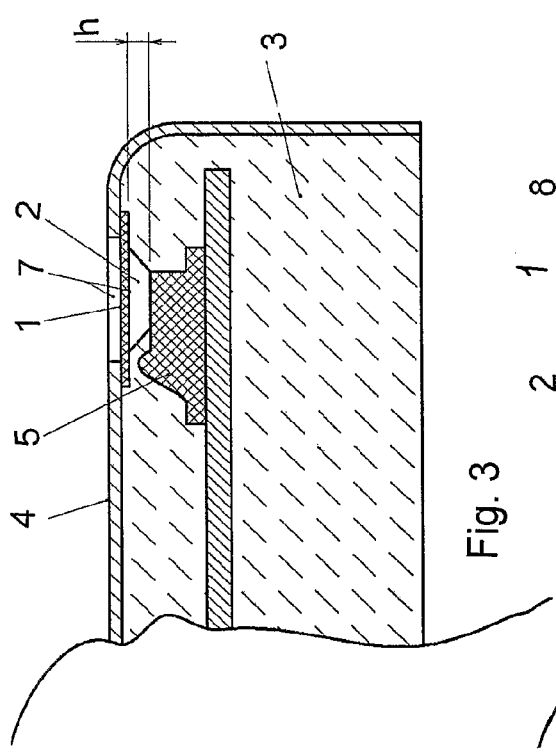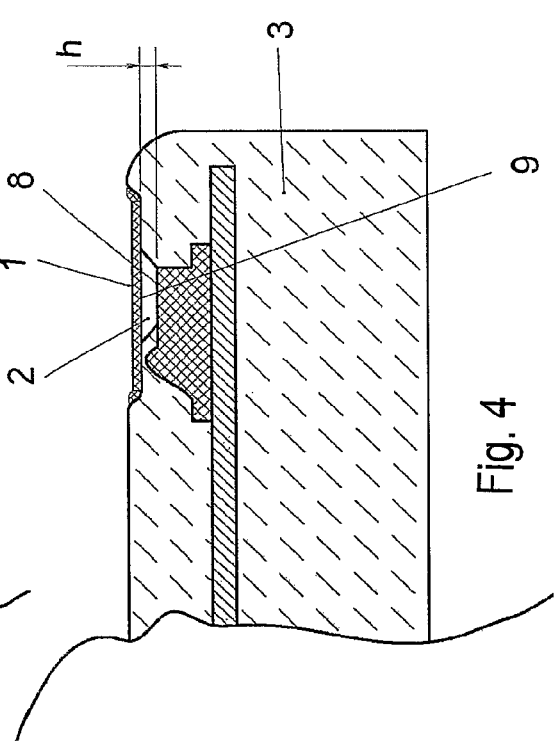

HUMIDITY SENSOR AND A METHOD FOR MANUFACTURING THE SAME

FIELD OF THE INVENTION

The present invention relates to a humidity sensor as well as to a method for manufacturing said humidity sensor.

BACKGROUND ART

Known humidity sensors of the type that detects the relative humidity of air, by absorbing water from the ambient into a polymer, where the principle of measuring is, to detect the change of the dielectric constant or conductivity of this polymer as a function of the relative humidity, has the implicit weakness, that they deteriorate over time, if they frequently are exposed to condensing conditions, moisture and dirt. As a consequence of this, most humidity sensors are equipped with some kind of protective encapsulation.

Humidity sensors of this type are nevertheless unsuited for use under conditions with condensation and moisture. The reason for this is, that the dead-space volume may be several thousand $mm^3$, allowing the amount of water condensing inside the encapsulation dead-space volume to accumulate and get so large, that it becomes a significant problem because of the irreversible damage it may cause on the sensing element.

The large amount of condensed water takes very long time to evaporate and diffuse out of the encapsulation. This is a major disadvantage for using this kind of humidity sensor in wet and condensing environment.

SUMMARY OF THE INVENTION

An object of the present invention is to wholly or partly overcome the above disadvantages and drawbacks of the prior art. More specifically, it is an object to provide a humidity sensor which may be used in wet and condensing environments.

These objects is achieved by means of the humidity sensor according to the appended claims.

Recent availability of sensor elements with small dimension makes it possible to construct humidity sensors with a very small dead-space volume, by small is in this context meant below 100 $mm^3$.

Furthermore, a practical shape for the dead-space volume like a truncated cone or a trumpet like duct may be advantageously, where a porous membrane covers the big end of that cone or duct and the sensor element is placed in the opposite smaller end. The cylindrical surface of the cone or trumpet tube is mainly made and formed of the moulding material and the hole in the external encapsulation may also be a part of this cylindrical surface. The height of the dead-space volume is made as small as possible reducing the volume accordingly. The area of the Teflon membrane is characterized by being large within practical limits, in order to maximize the effective area that water vapour is diffusing or breathing through.

According to the invention the humidity sensor is characterized by the combination of a small dead-space volume and a large membrane area, which improves the humidity sensors ability to respond quickly to changes of humidity concentration in the ambient air and by a small dead-space volume that only contains a little amount of water vapour that may condense within it. When there is condensed water in the dead space volume, the sensor element is saturated with water and detects 100% relative humidity, but when the relative humidity of the ambient air is less than 100%, the ambient is able quickly to absorb and remove water from the dead-space volume allowing the sensor element to recover from a saturated condition back to normal sensitivity. Within the inventive idea a ratio between an area of the membrane in relation to the dead-space volume may be larger than 1/5 ($mm^{-1}$), preferably larger than 1/3 ($mm^{-1}$), more preferably 1/2 ($mm^{-1}$), most preferably larger than 1/1 ($mm^{-1}$).

Accordingly, the invention relates to a humidity sensor, which is made robust in order to withstand water and condensing environment. It is characterized by embedding of a humidity sensor element into a moulding made of a thermoplastic material or a two component polyurethane epoxy or silicone casting which adheres to the internal surface of a metal or plastic encapsulation, housing or casing, shaped like a capsule or tube in which it is contained.

A small orifice in the encapsulation and the moulding leading to the sensing element, is covered by a porous Teflon membrane, which is glued to the external surface of the encapsulation. The sensor element, which is sensitive to the relative humidity of air, is indirectly exposed to the ambient atmosphere by diffusion of air through the porous membrane, which has the function to protect the sensor element by isolating it selectively from the ambient atmosphere.

The membrane which preferably is made of porous Teflon (PTFE), is permeable to air and gases like water vapour, but effectively blocks transfer of liquid water and dust particles including substances like oil drops, bacteria, etc.

Additionally, the humidity sensor according to the invention has a construction where the size of the volume between the membrane and the sensor element, is designed to be small in order to minimize the amount of water molecules that may condensate to liquid water and wet the sensor element in this volume. This volume between the membrane and the sensor element will further in this document be referred to as the dead-space volume.

According to the inventive idea, the dead-space volume is less than 100 $mm^3$, preferably less than 50 $mm^3$, more preferably less than 25 $mm^3$ and most preferably between 1-15 $mm^3$. Also the active membrane area may be greater than 10 $mm^2$. By using commercially available sensor elements and by reducing the dead-space volume by about 3 orders of magnitude compared to similar volumes found in traditional humidity sensors, with a protective encapsulation of the sensor element an expedient construction of the inventive humidity sensor is obtained.

The moulding material used in the invention may be a two-component polyurethane, epoxy or silicone material, which adheres to the internal surface of the external encapsulation. The moulding material may also be a thermo plastic material with low viscosity, which is suitable for low-pressure injection moulding of electronic components.

The advantage of the injection moulding is the short curing time of less than a minute. The invention also relates to a method for manufacturing the humidity sensor by a moulding process which in combination with a heating process is making the plastic moulding material adhere effectively to the inside of the metal encapsulation. Typically the moulding is made in two or more successive process steps, where the first step is a moulding of the PCB (Printed Circuit Board) with the sensor element and the associated signal processing electronics. In this first moulding the metal bushing(s) for the mounting hole(s) are also integrated, and a core in the mould shapes the orifice and the dead-space volume containing the sensor element. In the next process step the first moulding is placed inside a thin external metal encapsulation, which fits to the shape of the first moulding, and where an orifice gives access to the dead-space volume over sensor element. The metal encapsulation also has mounting holes that aligns with the holes in the bushings in the first cast and a hole in the side for the cable.

In a second heating process, the metal encapsulation is heated from the outside to a temperature that is high enough to melt the surface of the moulding material inside the encapsulation. This makes the moulding adhere to the inside surface of the encapsulation and make a tight lamination because the moulding material has the properties of a hot melting glue.

A further injection moulding may be necessary to make a nice plane filling of the bottom of the encapsulation, as the shrinking properties of the plastic material makes it impractical to make the mould in only one step.

BRIEF DESCRIPTION OF THE DRAWINGS

The invention and its many advantages will be described in more detail below with reference to the accompanying schematic drawings, which for the purpose of illustration show some non-limiting embodiments and in which FIG. 1 shows a humidity sensor with an encapsulation 4, a hole 11 with a bushing 10 for mounting the device and finally a PCB 6, on which the electronic components and the humidity sensor are mounted.

FIG. 2 shows details of FIG. 1, where the porous membrane 1 is glued on to the external encapsulation 4 and where the PCB 6 with the sensor element 5 are cast into a moulding compound 3, which is adhering to the inside of the external metal or plastic encapsulation 4.

FIG. 3 shows the same as FIG. 2 except for the membrane 1, which is placed between the encapsulation 4 or the moulding 3.

FIG. 4 shows the same as FIG. 2 except that the external encapsulation 4 is absent and the membrane 1 is glued directly on to the moulding compound 3, which together with the membrane 1, form the external surface of the humidity sensor.

All the figures are highly schematic and not necessarily to scale, and they show only parts which are necessary in order to elucidate the invention, other parts being omitted or merely suggested.

DESCRIPTION OF PREFERRED EMBODIMENTS

The humidity sensor according to invention reduces the water exposure to the sensor element 5, from condensing water vapour. This is achieved by making the dead-space volume 2 between the membrane 1 and the sensor element 5 as small as a few mm$^3$ which is a reduction of about typically 3 orders of magnitudes, compared to the dead-space volume of known humidity sensors. This construction leaves very little water in the dead-space volume 2 for possible condensing, and if condensing has taken place it allows the dead-space volume to evaporate the excess liquid water quickly out to the ambient through the relatively big membrane 1.

The membrane 1 may be placed between the external encapsulation 4 and the moulding 3 and glued to one or both of these.

The invention also provides a construction method of a humidity sensor which effectively encapsulates the sensor element 5 by a multi step moulding of the PCB 6 and the sensor element 5 in a thermo plastic compound 3. The first step of the moulding process is the moulding of the PCB 6, which is holding the sensor element 5 and one or more bushings 11. This primary moulding is then placed inside a protective encapsulation 4 where it fits precisely. For a few seconds the encapsulation is heated from the outside and this transfers just enough heat through the metal to melt the surface of the internal moulding 3 and make it glue efficiently to the inside of the hot external encapsulation 4 which is cooled down from the outside to allow the moulding 3 to cure again.

In order to achieve the gluing effect the plastic moulding material has properties similar to hot melting glue. Finally a last optionally moulding has the purpose of filling the external encapsulation 4 completely with moulding 3. These three moulding processes in combination, encapsulate the sensor element 5 hermetically, into a laminated cast of an outer metal encapsulation 4 and an internal plastic moulding 3, glued watertight together. The only access to the sensing element 5 is by gas diffusion through the hydrophobic and oleophobic porous Teflon membrane 1, which is fixed tightly to the metal encapsulation 4 by gluing it over the opening 7 of the conic or trumpet shaped dead-space volume 2. This construction provides a robust metal surface on the external side of the sensor that is exposed to the ambient atmosphere. The humidity sensor can be fastened on a smooth surface or wall, by a screw through the mounting hole 11, which is reinforced by the bushing 10, which hinders the force from the screw to deform the sensor and damage the internal PCB 6.

Although the invention above has been described in connection with preferred embodiments of the invention, it will be evident for a person skilled in the art that several modifications are conceivable without departing from the invention as defined by the following claims.

The invention claimed is:

1. A humidity sensor comprising a sensor element, a moulding comprising a thermoplastic material or a two-component polyurethane, epoxy or silicone casting and which is adapted to adhere to the sensor element, a dead-space volume, which is arranged in connection with the sensor element and which is covered by a membrane, said membrane is attached to an external surface of the moulding and is adapted to protect the sensor element from exposure to ambient moisture and dirt and allowing diffusion of ambient air gas molecules into the dead-space volume wherein the dead-space volume is less than 100 mm$^3$.

2. The humidity sensor according to claim 1, wherein the dead-space volume is less than 50 mm$^3$.

3. The humidity sensor according to claim 1, wherein the dead-space volume has a geometric shape of a truncated cone, said sensor element being situated at the most narrow end of the dead-space volume and said membrane being situated at the widest end of the dead-space volume, so that a maximum diffusion of water molecules through the membrane is obtained.

4. The humidity sensor according to claim 1, wherein an encapsulation is adapted to surround the moulding on one or more sides.

5. The humidity sensor according to claim 4, wherein the membrane is attached to an external surface of the encapsulation.

6. The humidity sensor according to claim 4, wherein the membrane is situated between the moulding and an internal surface of the encapsulation and is glued to one or both of these.

7. The humidity sensor according to claim 4, wherein the membrane is glued on to the encapsulation.

8. The humidity sensor according to claim 1, wherein the membrane is made of a hydrophobic and olephobic material.

9. The humidity sensor according to claim 1, wherein a ratio between an area of the membrane in relation to the dead-space volume is larger than 1/5 (mm$^{-1}$).

10. A method for manufacturing a humidity sensor according to claim 1 comprising the steps of:
- injecting moulding of a moulding, which is configured to hold a sensor element,
- placing the moulding inside a encapsulation, and
- heating the encapsulation for a few seconds from the outside, thus transferring heat through encapsulation for melting the surface of the internal moulding so that it adheres to the inside of the heated external encapsulation, which subsequently is cooled down from the outside to allow the moulding to cure.

11. The method according to claim 10, wherein additional moulding material is filled in the external encapsulation for completely filling the encapsulation.

* * * * *